United States Patent [19]
Witvliet

[11] Patent Number: 6,001,348
[45] Date of Patent: Dec. 14, 1999

[54] **NON-VIRULENT *MYCOPLASMA SYNOVIAE* AND VACCINE THEREOF**

[75] Inventor: Maarten Hendrik Witvliet, Oostrum, Netherlands

[73] Assignee: Akzo Nobel N.V., Arnhem, Netherlands

[21] Appl. No.: 08/985,669

[22] Filed: Dec. 5, 1997

[30] Foreign Application Priority Data

Dec. 5, 1996 [NL] Netherlands .......................... 96203441

[51] Int. Cl.$^6$ .......................... A01N 63/00; A01N 59/06; A61K 39/002; A61K 39/12
[52] U.S. Cl. .................. 424/93.1; 424/184.1; 424/264.1; 424/234.1; 424/214.1; 424/215.1; 424/816; 424/826; 424/93.3; 424/265.1; 424/698; 424/690; 424/691
[58] Field of Search ............................... 424/93.7, 184.1, 424/264.1, 234.1, 214.1, 215.1, 816, 826, 93.3, 265.1, 698, 690, 691

[56] References Cited

U.S. PATENT DOCUMENTS

| | | |
|---|---|---|
| 3,534,136 | 10/1970 | Dunlop et al. . |
| 3,917,819 | 11/1975 | Yoshioka et al. . |
| 4,115,195 | 9/1978 | Barth et al. . |
| 4,515,777 | 5/1985 | Apontoweil et al. . |
| 5,004,607 | 4/1991 | Ragland et al. . |
| 5,064,647 | 11/1991 | Storm . |
| 5,093,258 | 3/1992 | Cohen et al. . |
| 5,196,514 | 3/1993 | Avakian et al. . |
| 5,621,076 | 4/1997 | Kodama et al. . |

FOREIGN PATENT DOCUMENTS

| | | |
|---|---|---|
| 46843 | 6/1998 | Australia . |
| 0109942 | 5/1984 | European Pat. Off. . |
| 0307976 | 3/1989 | European Pat. Off. . |
| 0345021 | 12/1989 | European Pat. Off. . |
| 0846468 A1 | 6/1998 | European Pat. Off. . |
| WO 96/31613 | 10/1996 | WIPO . |

OTHER PUBLICATIONS

Droual et al. Avian Diseases, 36:803–807, 1992.
Kleven et al, Avian Diseases, 19/1:126–135, 1975.
Nonomura et al. Avian Diseases, 26/4:763–775, 1983.

*Primary Examiner*—Nita Minnifield
*Attorney, Agent, or Firm*—William M. Blackstone; Michael G. Sullivan

[57] ABSTRACT

The present invention provides NAD-independent *Mycoplasma synoviae* of strain MS1. The invention also refers to microbiological cultures comprising *Mycoplasma synoviae* of this strain. Next to this, the invention refers to live vaccines derived from these strains, for the protection of poultry against *Mycoplasma synoviae* infection. Furthermore, the invention provides methods for the preparation of such vaccines. Also, the use of NAD-independent *Mycoplasma synoviae* strains for the preparation of live vaccines for the protection of poultry against *Mycoplasma synoviae* infection is disclosed.

16 Claims, No Drawings

NON-VIRULENT *MYCOPLASMA SYNOVIAE* AND VACCINE THEREOF

BACKGROUND OF THE INVENTION

*Mycoplasma synoviae* is a mycoplasma that is highly infectious to poultry. *Mycoplasma synoviae* infection is a severe problem in the vast majority of broiler breeder and layer industries. It also often appears in turkey flocks.

Disease caused by *Mycoplasma synoviae* leads to a decrease in body weight gain and loss of egg production. Morbidity in both chickens and turkeys usually varies between 5–15%. Mortality in chickens is usually low, but may be significant in turkey flocks due to trampling and cannibalism.

Infectious synovitis was first seen at large scale primarily in chickens in growing birds between 4–12 weeks of age in broiler-growing regions in the USA between 1950 and 1960. During that time, the disease was for the first time described and associated with a mycoplasma (Olson et al.; Poult. Sci. 33: 1075 (1954) and Olson et al.; Am. J. Vet. Res. 17: 747–754 (1956)).

Transmission of the infection occurs through the respiratory tract. Natural infection is seen from one week of age in chickens and usually between 10–24 weeks in turkeys. *Mycoplasma synoviae* infection may occur as a subclinical upper respiratory infection, but can also lead to severe airsacculitis. In other cases, *Mycoplasma synoviae* becomes systemic and results in infectious synovitis, an acute to chronic infectious disease in chickens and turkeys. This disease is characterised by infection of the synovial membranes of joints and tendon sheaths, producing an exudative synovitis, tenovaginitis or bursitis. Especially problematic is the fact that during vaccination against Newcastle disease or Infectious Bronchitis (or other respiratory poultry pathogens), a standard procedure in almost all chicken-producing countries, animals carrying a *M. synoviae*-infection are also vaccinated. In these *M. synoviae* infected animals the ND- and IBV-vaccinations often trigger respiratory infection and air sac infection (Kleven et al.; Avian Dis. 16: 915–924 (1972), Springer et al.; Infect. Immun. 10: 578–589 (1974)). It is clear, that *M. synoviae* infection, both as a synovial infection and as a respiratory infection, causes great economic damage to the poultry industry. Therefore, efficient vaccines against *M. synoviae* would be highly appreciated.

So far only inactivated *Mycoplasma synoviae* vaccines are used in the field. U.S. Pat. No. 3,917,819 discloses an inactivated vaccine against mycoplasma infections. These vaccines however are expensive, since relatively large amounts of antigenic material are necessary to trigger a sufficient immune response. Moreover, all inactivated vaccines have to be manually applied by e.g. eye-drop or parenteral route, requiring individual handling of each individual animal. This is a very labour intensive method of vaccination. Live attenuated vaccines are more desirable, because they have several advantages over inactivated vaccines. First of all, they may comprise less antigenic material because they are self-replicating. Moreover, they give a better protection because they closely mimic the natural infection. As a basis for live *Mycoplasma synoviae* vaccines, live attenuated *Mycoplasma synoviae* strains are needed. Only one specific live attenuated strain has been described (Nonomura et al.; Avian Dis. 26: 763–775 (1982)) but no live attenuated vaccine based on this strain has been put on the market. The live attenuated strain by Nonomura, as well as wild-type strains, has the disadvantage, that it must be grown on culture medium containing Nicotinamide Adenine Dinucleotide. This is an expensive component, that can in addition not be sterilised by heating, thus making culture medium preparation more complex. NAD-independence is therefore a highly advantageous feature.

Strains that are adapted to nicotinamide (NIC) instead of NAD are described by DaMassa (DaMassa, A. J. and Adler H. E.; Avian Diseases 19: 544–555, (1975)). These strains however have the disadvantage that they have their original virulence, which makes them not suitable as a basis for live attenuated vaccines.

In addition, the live attenuated strain described by Nonomura, just like the inactivated vaccines, has the disadvantage that it must be administered by dropping into the nostrils of each individual animal. As mentioned before, this is a very labour intensive method of vaccination.

Therefore, a live attenuated strain effective if administered by spraying, and capable of growth on an NAD-free medium is highly desired.

SUMMARY OF THE INVENTION

It is an object of the present invention to provide such an NAD-independent live attenuated *Mycoplasma synoviae* strain. It is another object of the invention to provide vaccines based on such strains.

These objects are met by the present invention in that it provides a live attenuated *Mycoplasma synoviae* of strain MS1, deposited on Nov. 21, 1996 with the Collection Nationale de Cultures de Microorganismes of the Institut Pasteur, 25, Rue du Docteur Roux, 75724 Paris CEDEX 15, France, under No 1-1787.

This strain, that was derived from an NAD-dependent strain, has been adapted to growth on NAD-free mycoplasma growth medium.

The strain MS1 according to the present invention can be grown in modified Adler medium (H. E. Adler, R. Yamamoto and S. Bankowski, (1954) Am. J. Vet. Res. 15: 463–465) The modification consists in replacing Bacto PPLO broth by protease peptone (Difco), horse serum by porcine plasma, and by the addition of nicotinamide to a final concentration of 0.01%.

The present invention also relates to a microbiological culture comprising live attenuated *Mycoplasma synoviae* of the strain according to the present invention. Such a microbiological culture can easily be obtained by preparing a culture medium as described above, and inoculating this medium with a few mycoplasmas of the deposited strain. It is obvious, that also other suitable media known in the art can be used for growing the strain according to the present invention. Also, although the strain of the present invention is NAD-independent, it is still possible to add NAD to the culture medium if desired.

The present invention also provides live vaccines for the protection of poultry against *Mycoplasma synoviae* infection that have the unique feature that they comprise live attenuated *Mycoplasma synoviae* according to the present invention. Vaccines according to the invention can be given to animals from one day of age on. Vaccination against another type of mycoplasma; *M. gallisepticum* is given at 6 weeks of age, and can thus efficiently be combined with *M. synoviae* vaccine according to the invention. Therefore, a vaccine according to the invention can be given efficiently at 6 weeks of age.

In another embodiment, the vaccine according to the present invention comprises at least one other antigen from a virus or micro-organism pathogenic to poultry. Such a combination vaccine has the advantage that it provides immunisation against multiple pathogens with one single vaccination.

The antigen may be a protein, a glycoprotein, a polysaccharide, a lipopolysaccharide or any other antigen or any combination thereof, that is capable to induce a response in the immune system.

Also, whole live attenuated or inactivated organisms can be used as antigenic material.

In particular, the other poultry pathogens are selected from the group consisting of Infectious Bronchitis virus, Newcastle Disease virus, Infectious Bursal Disease (Gumboro), Chicken Anaemia agent, Avian Reovirus, Chicken Poxvirus, Avian Encephalomyelitis virus, Turkey Rhinotracheitis virus, *Mycoplasma gallisepticum, Haemophilus paragallinarum* (Coryza), *Pasteurelia multocida* (Fowl Cholera), *Omithobactenum rhinotracheale* and *Escherichia coli*.

The vaccine can be given in all manners known for the administration of live vaccines. It can e.g. be given intraocularly, intranasally, intratracheally or orally. Parenteral administration is also possible. Since transmission of the infection occurs via the respiratory tract, vaccination trough the respiratory tract closely mimics the natural way of infection. A specific advantage of the live vaccine based on *Mycoplasma synoviae* of strain MS1 is, that it allows spray-vaccination. Spray-vaccination is the easiest way of administration when vaccinating through the respiratory tract: it allows the vaccination of large numbers of animals at the same time by simply nebulising the vaccine strain in the presence of the animals to be vaccinated. The easiest way of spray-vaccination is spraying the live vaccine with a nebuliser. Such a nebuliser provides microscopic droplets comprising the live vaccine. If these vaccine-droplets are inhaled by the animals to be vaccinated they penetrate the respiratory tract, and thus advantageously mimic the natural infection. Any kind of nebuliser commonly used for vaccination of poultry will do. This method is also a very efficient one because time-consuming individual handling of the animals to be vaccinated is not necessary. Therefore, in an even more preferred form, vaccines according to the invention comprise a carrier that is suitable for spray-vaccination. Such a carrier may be as simple as water, or can be e.g. a physiological salt solution or culture medium. A very suitable amount of *Mycoplasma synoviae* for spraying in an isolator of 1 cubic metre varies between $10^6$ and $10^{11}$ Colour Changing Units (CCU). Optionally, one or more compounds having adjuvant activity may be added to the vaccine. Adjuvantia are non-specific stimulators of the immune system. They enhance the immune response of the host to the invading pathogen. Therefore, in a still even more preferred form, the vaccines according to the present invention comprises an adjuvant.

Examples of adjuvantia known in the art are Freunds Complete and Incomplete adjuvant, vitamin E, non-ionic block polymers, muramyldipeptides, ISCOMs (immune stimulating complexes, cf. for instance European Patent EP 109942), Saponins, mineral oil, vegetable oil, and Carbopol (a homopolymer).

Adjuvantia, specially suitable for mucosal application are e.g. the *E. coli* heat-labile toxin (LT) or Cholera toxin (CT).

Other suitable adjuvants are for example aluminium hydroxide, phosphate or oxide, oil-emulsions (e.g. of Bayol $F^{(R)}$ or Marcol 52$^{(R)}$, saponins or vitamin-E solubilisate.

The live vaccine according to the present invention can be prepared by mixing *Mycoplasma synoviae* of strain MS1 with a pharmaceutically acceptable carrier. Often, the vaccine is additionally mixed with stabilisers, e.g. to protect degradation-prone polypeptides from being degraded, to enhance the shelf-life of the vaccine, or to improve freeze-drying efficiency. Useful stabilisers are i.a. SPGA (Bovamik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates. It goes without saying, that other ways to stabilise the vaccine by adding compounds are also embodied in the present invention.

The vaccine according to the present invention can be kept in storage using methods known in the art for storing live vaccines. Storage can e.g. be done at sub-zero temperature.

Freeze-drying also is a known and suitable method for the conservation of live vaccines. Freeze-drying has the advantage, that it stabilises the vaccine so that it can be kept in stock at temperatures well above those necessary to keep non-freeze-dried stocks.

The live vaccine according to the present invention can be freeze-dried very efficiently, especially when it is mixed with stabilisers such as those mentioned above before freeze-drying.

Therefore, in the most preferred embodiment, the live vaccine is in a freeze-dried form. In order to make the freeze-dried vaccine ready for use, it suffices to add water to the freeze-dried vaccine.

In addition, antibiotics such as ampicillin or tertracyclin may be added to the vaccine.

Furthermore, the invention provides methods for the preparation of live *Mycoplasma synoviae* vaccines. Such methods comprise mixing *Mycoplasma synoviae* according to the present invention with a pharmaceutically acceptable carrier. Pharmaceutically acceptable carriers include carriers that are not harmful to health and in addition carriers where the negative effect on health is counterbalanced by the beneficial effect of vaccination. A pharmaceutically acceptable carrier is e.g. be a physiological salt solution.

Further the invention relates to the use of *Mycoplasma synoviae* according to the present invention for the preparation of live vaccines for the protection of poultry against *Mycoplasma synoviae* infection.

DETAILED DESCRIPTION OF THE INVENTION

EXAMPLES

Example 1: Preparation of Vaccine Batch.

One ampoule comprising $10^7$ CCU of lyophilised MS1 was used to inoculate 20 ml of modified Adler's medium (see above). After overnight incubation at 37° C., 1:10 and 1:100 subcultures were prepared in 100 ml of medium; followed by overnight incubation at 37° C. Then, the 1:10 and 1:100 subcultures were mixed, and used as a spray vaccine.

Example 2: Safety-Tests and Vaccination Challenge Tests.

In order to test the safety of the strain MS1, chickens were experimentally vaccinated as follows:

Chickens were spray vaccinated using a paint sprayer. The sprayer was filled with 100 ml of the above described vaccine. About 100 ml of the vaccine was sprayed per 1 m$^3$ isolator.

About 10 ml of the vaccine was sprayed per animal.

Experimental Animals

Thirty-five SPF laying hens (Intervet) and thirty-five Hyline brown laying hens (Interbroed) were housed in isolators. The animals were observed daily.

Experimental Design

Six groups of chickens were used:

| Group | Type (n)        | MS1 vaccination | F10 challenge |
|-------|-----------------|-----------------|---------------|
| A     | SPF (10)        | −               | −             |
| B     | SPF (15)        | +               | +             |
| C     | SPF (10)        | −               | +             |
| D     | Hyline brown (10) | −             | −             |
| E     | Hyline brown (15) | +             | +             |
| F     | Hyline brown (10) | −             | +             |

At 6 weeks of age, the animals in groups B and E were spray vaccinated with a MS1 culture according to Example 1. Ten days later, 5 animals of groups A, B, D and E were necropsied to evaluate the safety of MS1.

Challenge

The chickens in groups B, C, E and F were challenged with the virulent F10 strain at 9 weeks of age, followed by necropsy of all animals 10 days later.

The animals were primed by administration of a Newcastle disease strain three days before *M. synoviae* challenge.

*M. synoviae* strain F10 was obtained from Dr. S. H. Kieven, University of Georgia, Athens Ga. and cultured in Frey's medium (Frey et al.; Am. J. Vet. Res. 29: 2163–2171 (1963)). One ampoule of F10 (26-10-1995 P2, 1 ml, stored frozen at −70° C.) was used to inoculate 10 ml of medium. After 48 h of incubation at 37° C., 1:10, 1:100 and 1:1000 subcultures were made in 100 ml of medium and incubated overnight at 37° C. The challenge culture was prepared by mixing the 1:10 and 1:100 subcultures, and administered by paint sprayer (100 ml per isolator). The CCU count of the challenge mixture was determined. The animals in groups A and D received the ND virus followed by a 50 ml spray of Frey's medium 3 days later.

Serology

Serum samples were taken 1 week before vaccination, at the time of challenge and at necropsy. The samples were tested for *M. synoviae* agglutinating antibodies with *M. synoviae* antigen Nobilis (Intervet, batch MSG508).

CCU Determination

The numbers of viable organisms in the *M. synoviae* cultures were titrated by preparing serial 10-fold dilution's in 1 ml of culture medium, followed by 10 days of incubation at 37° C. The highest dilution giving a colour change of the indicator in the medium was used to calculate CCU/ml.

Post-Mortem Examination

At necropsy, the chickens were examined for signs of tracheitis and synovitis, and airsacculitis was scored as described (Kleven et al.; Avian Dis. 16: 915–924 (1972)):
0: no lesions
1: slight cloudiness of the air sac membranes
2: thickened membranes with small accumulations of cheesy exudate
3: thickened membrane with large accumulations of cheesy exudate in 1 air sac
4: as in 3, but lesions found in 2 airsacs or more Trachea, air sac and hock joint swabs were cultured for *M. synoviae*. Re-isolation of *M. synoviae* was confirmed by PCR (Lauerman et al.; Avian Dis. 37: 829–834 (1993)).

RESULTS

Safety of MS1

All animals were tested for antibodies against *M. synoviae* 7 days before vaccination, and no positive reactors were found. At 6 weeks of age, the chickens in groups B and E were spray vaccinated with a MS1 culture containing $10^9$ CCU/ml. No clinical abnormalities were observed following vaccination. Ten days post vaccination, 5 animals of groups B and E and 5 unvaccinated controls of groups A and D were necropsied. No signs of trachetis, airsacculitis (score=0), synovitis or other abnormalities were found. All 15 chickens in group E and 13 out of 15 in group B had developed antibodies to *M. synoviae* at 10 days post vaccination as measured by serum plate agglutination (Table 1).

Efficacy of MS1

At the time of challenge (i.e. 21 days post vaccination), antibody levels in vaccinated chickens were high (Table 1). For the challenge of the chickens in groups B, C, E and F, an F10 culture containing $10^8$ CCU/ml was used. As shown in Table 2, airsacculitis scores were significantly lower in the vaccinated chickens (groups B and E) than in challenge control chicken. Tracheits was observed in 2 group A chickens and 2 chickens of group C. Swollen spleens were found in 2 animals in group A, 1 in group B, 7 in group C, 1 in group D and 5 in group F. No animals in group E had swollen spleens. Two animals in group C and 1 in group F suffered from pneumonia.

*M. synoviae* could be re-isolated from the tracheas and airsacs of animals in all challenged groups (Table 3). No differentiation between vaccine or challenge strain re-isolation was made. Nevertheless, no *M. synoviae* was isolated from hock joints of vaccinated chickens, compared to positive cultures in 1 animal in group C and 3 in group F. No other species of mycoplasma were isolated.

Table 1: Serum plate agglutination results. Groups B and E were vaccinated with MS1 at 6 weeks of age (t=0), C and F were unvaccinated controls. Groups B, C, D and E were challenged with F10 on t=21 and necropsied on t=31d. Sera were tested with *M. synoviae* antigen Nobilis (maximum agglutination score: ++++).

| Group B | t = −7d | t = 10d | t = 21d | t = 31d | Group C | t = 21d | t = 31d |
|---------|---------|---------|---------|---------|---------|---------|---------|
|         | −       | ++±     | +++±    | ++++    |         | −       | +++     |
| Group E | t = −7d | t = 10d | t = 21d | t = 31d | Group F | t = 21d | t = 31d |
|         | −       | +++±    | +++±    | +++±    |         | −       | ++±     |

TABLE 2

Airsacculitis score[1] 10 d after F10 challenge.
A,D: unvaccinated and unchallenged;
B,E: vaccinated and challenged;
C,F: uncaccinated and challenged

| | SPF | | | Hyline-brown | | |
|---|---|---|---|---|---|---|
| Animal | A (cont) | B (vac) | C (chall) | D (cont) | E (vac) | F (chall) |
| 1 | 1 | 1 | 3 | 1 | 1 | 3 |
| 2 | 0 | 1 | 3 | 0 | 0 | 3 |

TABLE 2-continued

Airsacculitis score[1] 10 d after F10 challenge.
A,D: unvaccinated and unchallenged;
B,E: vaccinated and challenged;
C,F: uncaccinated and challenged

| | SPF | | | Hyline-brown | | |
|---|---|---|---|---|---|---|
| Animal | A (cont) | B (vac) | C (chall) | D (cont) | E (vac) | F (chall) |
| 3 | 1 | 4 | 3 | 0 | 1 | 1 |
| 4 | 1 | 1 | 2 | 0 | 1 | 1 |
| 5 | 0 | 1 | 2 | 1 | 1 | 3 |
| 6 | | 2 | 2 | | 3 | 3 |
| 7 | | 1 | 4 | | 1 | 3 |
| 8 | | 1 | 3 | | 0 | 3 |
| 9 | | 1 | 4 | | 1 | 1 |
| 10 | | 0 | | | | 3 |
| Mean | 0.6 | 1.3[b] | 2.9 | 0.4 | 1.0[b] | 2.4 |

[a]maximum score: 4
[b]significantly (p < 0.01) different from unvaccinated challenged control group (Kruskal-Wallis test)

TABLE 3

M. synoviae re-isolation rates

| | SPF | | | Hyline-brnwn | | |
|---|---|---|---|---|---|---|
| | A | B | C | D | E | F |
| trachea | nd[a] | 8/10 | 9/9 | 0/5 | 7/9 | 10/10 |
| air sac | nd | 5/10 | 4/9 | 0/5 | 3/9 | 9/10 |
| hock joint | nd | 0/10 | 1/9 | 0/5 | 0/9 | 3/10 |

[a]nd: not done

Example 3: Efficacy of Vaccine in Response to the Dose Given.

In order to tests the efficacy of the vaccine over a large range of doses, the following experiment was done:
Experimental Design
Four groups of chickens were used:

| Group | n | vaccination | F10 challenge |
|---|---|---|---|
| A | 10 | MS1 (1:100) | + |
| B | 9 | MS1 (1:10,000) | + |
| C | 10 | — | + |
| D | 5 | — | − |

At 6 weeks of age, the animals in groups A and B were spray vaccinated with an MS1 vaccine. Three weeks post vaccination, the animals in groups A, B and C were challenged with the virulent F10 strain after priming with ND virus as described above. All chickens were necropsied 10 days post challenge.
Experimental Animals
Thirty four SPF laying hens (Intervet) were housed in isolators. The animals were observed daily. One of the group B and one of the group C animals died before challenge.
Vaccination
Vaccine was prepared by lyophilization of a culture of strain MS1. Before spray vaccination, the content of 1 vial of lyophilized vaccine was resuspended in 100 ml of phosphate buffered saline solution (1:100 diluted vaccine). From this vaccine a 1:100 dilution was prepared in phosphate buffered saline solution (1:10,000 diluted vaccine). Chickens were vaccinated by fine spray (100 ml of vaccine dilution per isolator). The MS1 concentrations in the final vaccine dilutions were determined by CCU count.

RESULTS

The chickens were vaccinated with vaccines containing $10^6$ CCU/ml (group A) and $10^3$ CCU/ml (group B). Three weeks post vaccination the vaccinated chickens and unvaccinated controls were challenged with a M. synoviae F10 culture containing $10^7$ CCU/ml. At necropsy, protection against airsacculitis was observed in both vaccinated groups (Table 4).
Table 4: Airsacculitis score 10 d after F10 challenge
A: vaccinated at $10^6$ CCU/ml; B: vaccinated at $10^3$ CCU/ml; C: unvaccinated and challenged; D: unvaccinated and unchallenged.

TABLE 4

Airsacculitis score 10 d after F10 challenge
A: vaccinated at $10^6$ CCU/ml; B: vaccinated at $10^3$ CCU/ml; C: unvaccinated and challenged; D: unvaccinated and unchallenged.

| | Group | | | |
|---|---|---|---|---|
| Animal | A (1:100 vac) | B (1:10,000 vac) | C (chall) | D (cont) |
| 1 | 2 | 0 | 3 | 0 |
| 2 | 1 | 2 | 1 | 0 |
| 3 | 2 | 3 | 3 | 0 |
| 4 | 2 | 1 | 2 | 0 |
| 5 | 2 | 2 | 2 | 0 |
| 6 | 1 | 2 | 3 | |
| 7 | 0 | 1 | 2 | |
| 8 | 1 | 2 | 3 | |
| 9 | 1 | | 2 | |
| 10 | 1 | | | |
| Mean | 1.3[a] | 1.6[b] | 2.3 | 0 |

[a]: significantly (p<0.01) different from unvaccinated challenged control group [b]: p=0.10

CONCLUSION

The NAD-independent strain according to the present invention was a-virulent for 6 weeks old chickens after spray vaccination, demonstrated by the absence of any clinical abnormalities at necropsy 10 days post vaccination with a culture containing $10^9$ CCU/ml. Challenge with a culture of the virulent F10 strain at $10^8$ CCU/ml at the age of 9 weeks on the other hand resulted in severe airsacculitis in non-vaccinated chickens at 10 days post challenge.

Protection against challenge with the F10 strain was found in both SPF and commercial Hyline brown chickens, in a very broad dose-range. Airsacculitis scores were reduced, and no *M. synoviae* was isolated from the joints of vaccinated birds. The number of birds showing megalosplenia was also higher in the unvaccinated challenged controls. It can therefore be concluded that vaccines based on the *Mycoplasma synoviae* strain according to the present invention are safe and efficacious.

I claim:

1. An NAD-independent live attenuated *Mycoplasma synoviae* having the identifying characteristics of the strain MS1, which is deposited at the CNCM under Accession No. 1-1787.

2. A microbiological culture comprising the live attenuated *Mycoplasma synoviae* of claim 1 in a culture medium.

3. A vaccine for the protection of poultry against *Mycoplasma synoviae* infection, which comprises the live attenuated *Mycoplasma synoviae* of claim 1 and a pharmaceutically acceptable carrier.

4. The vaccine of claim 3, further comprising at least one other antigen from a microorganism or virus pathogenic to poultry.

5. The vaccine of claim 4, wherein the microorganism or virus is selected from the group consisting of Infectious Bronchitis virus, Newcastle Disease virus, Infectious Bursal Disease virus, Chicken Anaemia agent, Avian Reovirus, Chicken Poxvirus, Avian Encephalomyelitis virus, Turkey Rhinotracheitis virus, *Mycoplasma gallisepticum, Haemophilus paragallinarum, Pasteurella multocida, Ornithobacterium rhinotracheale* and *Escherichia coli.*

6. The vaccine of claim 3, which further comprises a carrier suitable for spray vaccination.

7. The vaccine of claim 3, further comprising an adjuvant.

8. The vaccine of claim 3, which is in a freeze-dried form.

9. A method for the protection of poultry against *Mycoplasma synoviae* infection comprising administering an effective amount of the vaccine of claim 3.

10. The method of claim of claim 9 wherein the vaccine is administered by spraying.

11. A method for the preparation of the vaccine for the protection of poultry against *Mycoplasma synoviae* infection, comprising mixing the *Mycoplasma synoviae* of claim 1 with a pharmaceutically acceptable carrier.

12. The vaccine of claim 4, which further comprises a carrier suitable for spray vaccination.

13. The vaccine of claim 4, further comprising an adjuvant.

14. The vaccine of claim 5, which further comprises a carrier suitable for spray vaccination.

15. The vaccine of claim 5, further comprising an adjuvant.

16. The live attenuated *Mycoplasma synoviae* of claim 1, which is the strain MS1 deposited at the CNCM under Accession No. 1-1787.

* * * * *

UNITED STATES PATENT AND TRADEMARK OFFICE
CERTIFICATE OF CORRECTION

PATENT NO. : 6,001,348
DATED : December 14, 1999
INVENTOR(S) : M.H. WITVLIET

It is certified that error appears in the above-identified patent and that said Letters Patent is hereby corrected as shown below:

Claim 10, column 9, line 16, please delete the second instance of "of claim".

In Table 2, column 6, line 60, please delete "uncaccinated" and insert --unvacinnated--.

Column 7, line 6, please delete "uncaccinated" and insert --unvaccinated--.

Signed and Sealed this

Eighteenth Day of July, 2000

Attest:

Q. TODD DICKINSON

Attesting Officer          Director of Patents and Trademarks